United States Patent
Patel et al.

(10) Patent No.: US 9,827,271 B2
(45) Date of Patent: Nov. 28, 2017

(54) METHODS AND DEVICES FOR LUNG VOLUME REDUCTION WITH EXTRACELLULAR MATRIX MATERIAL

(71) Applicant: Cook Biotech Incorporated, West Lafayette, IN (US)

(72) Inventors: Umesh H. Patel, West Lafayette, IN (US); Bhavin Shah, West Lafayette, IN (US); Michelle Chutka, West Lafayette, IN (US)

(73) Assignee: Cook Biotech Incorporated, West Lafayette, IN (US)

(*) Notice: Subject to any disclaimer, the term of this patent is extended or adjusted under 35 U.S.C. 154(b) by 0 days.

(21) Appl. No.: 14/210,815

(22) Filed: Mar. 14, 2014

(65) Prior Publication Data

US 2014/0271472 A1 Sep. 18, 2014

Related U.S. Application Data

(60) Provisional application No. 61/789,399, filed on Mar. 15, 2013.

(51) Int. Cl.

| | |
|---|---|
| A61K 38/39 | (2006.01) |
| A61K 35/38 | (2015.01) |
| A61K 9/00 | (2006.01) |
| A61K 51/04 | (2006.01) |
| A61L 31/00 | (2006.01) |
| A61B 17/12 | (2006.01) |
| A61L 24/00 | (2006.01) |

(52) U.S. Cl.
CPC ........ *A61K 35/38* (2013.01); *A61B 17/12104* (2013.01); *A61K 9/007* (2013.01); *A61K 51/0402* (2013.01); *A61L 24/0005* (2013.01); *A61L 31/005* (2013.01); *A61L 2430/36* (2013.01); *A61L 2430/40* (2013.01)

(58) Field of Classification Search
CPC .... A61K 38/39; A61K 51/0402; A61L 31/005
See application file for complete search history.

(56) References Cited

U.S. PATENT DOCUMENTS

| 7,468,350 B2 | 12/2008 | Gong et al. |
|---|---|---|
| 7,654,998 B1 | 2/2010 | Ingenito |
| 8,021,692 B2 | 9/2011 | Hiles et al. |
| 8,192,763 B2 * | 6/2012 | Johnson ............... A61L 27/3604 424/423 |
| 2003/0018327 A1 | 1/2003 | Truckai et al. |
| 2004/0047855 A1 * | 3/2004 | Ingenito ............... A61K 38/363 424/94.63 |
| 2004/0091543 A1 | 5/2004 | Bell et al. |
| 2005/0196344 A1 * | 9/2005 | McCutcheon ............ A61F 5/00 424/45 |
| 2005/0281739 A1 | 12/2005 | Gong et al. |
| 2008/0028135 A1 | 1/2008 | Rajan et al. |
| 2008/0281352 A1 | 11/2008 | Ingenito et al. |
| 2009/0318934 A1 | 12/2009 | Johnson et al. |
| 2009/0326577 A1 * | 12/2009 | Johnson ............. A61B 17/0057 606/213 |

FOREIGN PATENT DOCUMENTS

| WO | WO 01/02042 A1 | 1/2001 |
|---|---|---|
| WO | WO 01/13908 A2 | 3/2001 |
| WO | WO 2007/090150 A2 | 6/2007 |

OTHER PUBLICATIONS

Mo et al., Soft tissue adhesive composed of modified gelatin and polysaccharides, J Biomater Sci Polym Ed. 2000;11(4):341-51 (abstract).*
http://pulmonary.templehealth.org/content/upload/AssetMgmt/documents/LVRS.pdf, "Newer Techniques of non-surgical lung volume reduction", Temple Lung Center, last printed Mar. 19, 2015.
Ingenito, Edward P. et al., "Bronchoscopic Lung Volume Reduction Using Tissue Engineering Principles", Am. J. Respir. Crit. Care Med. vol. 167, pp. 771-778, 2003.

* cited by examiner

*Primary Examiner* — Michael G Hartley
*Assistant Examiner* — Nabila Ebrahim
(74) *Attorney, Agent, or Firm* — Woodard Emhardt Moriarty McNett & Henry LLP

(57) ABSTRACT

Lung volume reduction by isolating a target lung portion from the rest of the lung with a mass of extracellular matrix ("ECM") material. The procedure can be performed by locating a tube within the lumen of an airway to be obstructed and depositing an amount of flowable or other ECM in the open space until the lumen is occluded. Optionally, the procedure may be performed by delivering a plug substantially comprised of ECM material into the lumen of an airway to be obstructed. Further optionally, the ECM plug may include a one-way valve to allow air and mucous to escape from the isolated lung portion.

23 Claims, 5 Drawing Sheets

METHODS AND DEVICES FOR LUNG VOLUME REDUCTION WITH EXTRACELLULAR MATRIX MATERIAL

CROSS REFERENCE TO RELATED APPLICATIONS

This application claims the benefit of U.S. Provisional Application Ser. No. 61/789,399, filed on Mar. 15, 2013, which is incorporated herein by reference in its entirety.

BACKGROUND

The present invention generally relates to medical methods and devices, and in certain of its embodiments to methods and devices useful to reduce lung volume.

Chronic obstructive pulmonary disease ("COPD") refers to chronic bronchitis and emphysema, a pair of two commonly co-existing diseases of the lungs in which the airways become narrowed. This leads to a limitation of the flow of air to and from the lungs causing shortness of breath. In contrast to asthma, the limitation of airflow is poorly reversible and usually gets progressively worse over time. COPD is caused by noxious particles or gas, most commonly from tobacco smoking, which triggers an abnormal inflammatory response in the lung. The inflammatory response in the larger airways is known as chronic bronchitis, which is diagnosed clinically when people regularly cough up sputum. In the alveoli, the inflammatory response causes destruction of the tissues of the lung, a process known as emphysema. The natural course of COPD is characterized by occasional sudden worsenings of symptoms called acute exacerbations.

Surgery is sometimes helpful for certain COPD and emphysema patients. A bullectomy is the surgical removal of a bulla, a large air-filled space that can compress the surrounding, more normal lung. In lung volume reduction surgery, parts of the lung that are particularly damaged by emphysema are removed allowing the remaining, relatively good lung to expand and work better. Conventional lung reduction surgery involves surgical resection of the most severely affected areas of emphysematous, non-bullous lung. This is a surgical option involving a mini-thoracotomy for patients suffering end stage COPD due to underlying emphysema, and has been reported to improve lung elastic recoil as well as diaphragmatic function.

Conventional lung reduction surgery is, however, traumatic. The surgery is different than other surgeries in that it should not be considered a single procedure. There is an extensive pre- and post-operative rehabilitation program which needs to be followed for maximal effect. Some general surgery complications include: fever, wound infections, wound hematomas, postoperative fatigue, and tachycardia. The main complication of lung volume reduction surgery is an air leak. Normally there is a vacuum between the ribs and the lungs which helps to make the lungs expand and fill with air when the chest wall expands. If an air leak allows air in the potential space between the ribs and lungs then the vacuum effect is gone and the lung sags. This makes it very difficult to inflate the lungs and perform gas exchange. For these reasons, it is desirable to provide improved and/or alternative methods and devices for performing lung volume reduction.

SUMMARY

In one aspect, the present invention provides a method for lung volume reduction by delivering an extracellular matrix material to an airway of a lung. The method can include locating a tube in the lumen of the airway to be obstructed and delivering a material from the tube that includes extracellular matrix material in a sufficient amount to reduce the volume of the lung. The extracellular matrix material can be receptive to tissue ingrowth from the patient and can be resorbed over time as it is replaced by ingrown patient tissue.

In another aspect, the present invention provides a method that includes locating a tube in the lumen of the airway to be obstructed and delivering a flowable composition of extracellular matrix material from the tube. The flowable composition of extracellular matrix material can include a hydrolyzate composition of an extracellular matrix, preferably that is or forms a gel, a comminuted extracellular matrix material suspended in a liquid carrier, or a combination thereof.

In another aspect, the present invention provides a method that includes delivering a plug comprising extracellular matrix material into a lumen of a lung airway to be obstructed. The plug can in some variants include a one-way valve that allows air and mucous to escape from the isolated lung portion.

In another aspect, the present invention provides methods and devices to block a primary bronchus, to block a secondary bronchus, to block a tertiary bronchus, and/or to block bronchiols, that employ an extracellular matrix material.

In another aspect, the present invention provides plugs to isolate a target lung portion from the rest of the lung. The plugs comprise an extracellular matrix material.

In another aspect, the present invention provides the present invention provides a method for lung volume reduction by delivering into the lung a composition including an extracellular matrix material and a radiopaque material. The method can include locating a tube in the lumen of the airway to be obstructed and delivering a material from the tube that includes extracellular matrix material and a radiopaque material.

In all embodiments described above and elsewhere herein, (i) the extracellular matrix material(s) utilized can have any feature, or any combination of features, described herein for extracellular matrix material; and/or (ii) the airway portion of the lung into which the extracellular matrix material(s) is introduced can be treated to initiate a healing response, potentially with bleeding, for example by debridement with a brush or other suitable instrument.

Additional embodiments as well as features and advantages of the invention will be apparent to those of ordinary skill in the art from the descriptions herein.

DETAILED DESCRIPTION

Figure 1:
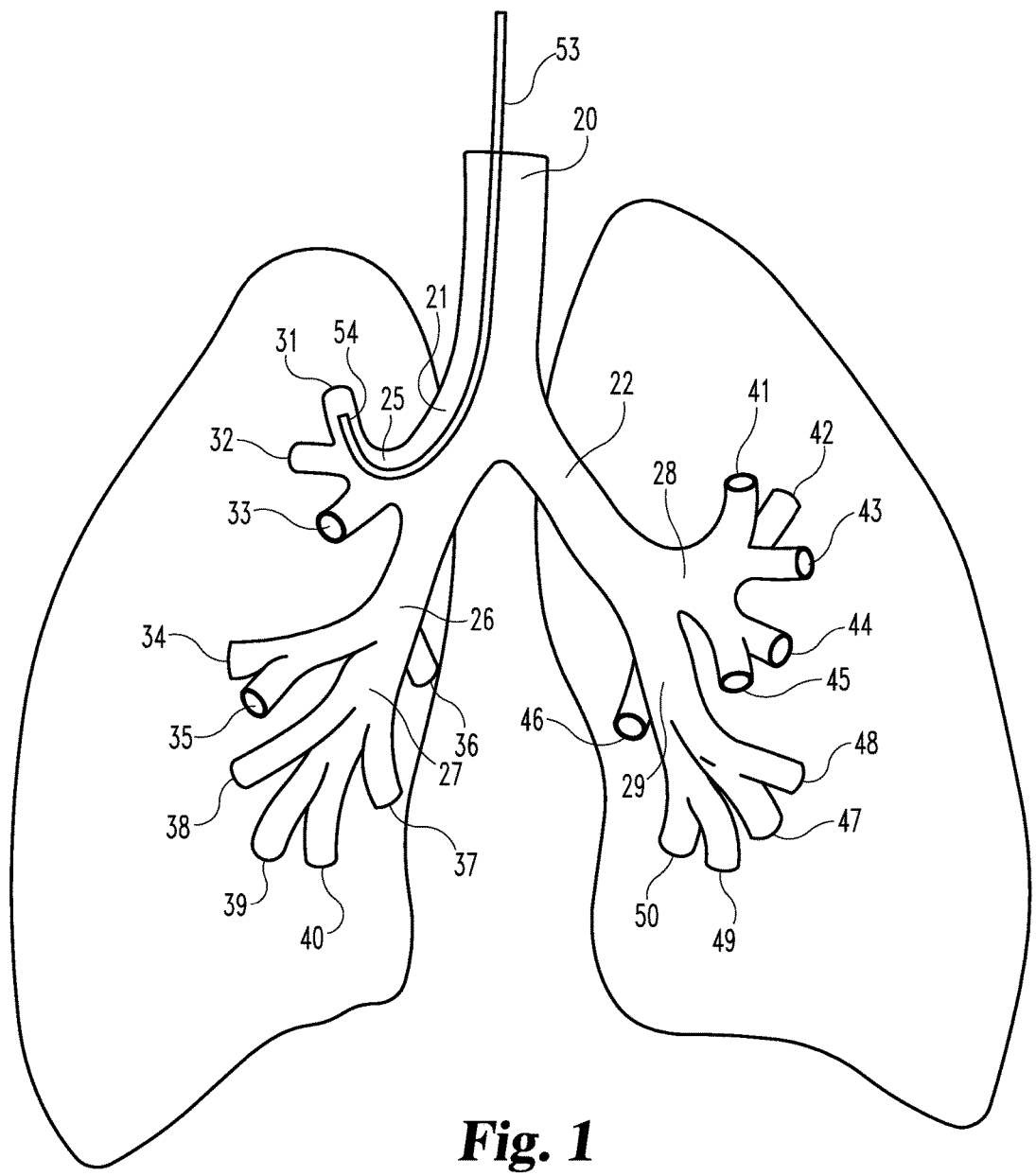
FIG. 1 is an abbreviated view of the bronchial tree and an illustration of bronchoscope accessing the lumen of a tertiary bronchus.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

Various embodiments of the invention provide for lung volume reduction by eliminating target lung tissue segments from the operative lung by plugging the airway that delivers and/or returns air to the target segment with a material that includes an extracellular matrix (ECM) material.

Extracellular matrix (ECM) materials, including those derived from submucosa and other tissues, are known tissue graft materials used in these medical applications. See, e.g., U.S. Pat. Nos. 4,902,508, 4,956,178, 5,281,422, 5,372,821, 5,554,389, 6,099,567, 6,206,931, 6,379,710, 4,361,552 and WO 03/002165, each of which is hereby incorporated herein by reference in its entirety. These materials can be derived from a variety of biological sources including, for example, small intestine, stomach, liver, amnion, the urinary bladder, skin, pericardium, peritoneum, dura mater, fascia, renal capsule, and the like.

ECM materials for use in the invention can be processed using methods that decrease the content of undesired components of the source tissue such as cells, nucleic acid, lipids and/or immunoglobulins such as IgA, while retaining substantial levels of desired components from the source tissue such as growth factor(s) (e.g. Fibroblast Growth Factor-2), proteoglycans and/or glycosaminoglycans (GAGS). Such treatments can be performed with detergent, basic medium, liquid organic solvent, and/or disinfecting solution, for example as described in U.S. patent application Ser. No. 12/178,321 filed Jul. 23, 2008, published Nov. 20, 2008 as US20080286268, the disclosure of which is specifically incorporated herein by reference in its entirety Further in this regard, the ECM starting material can be treated with a mild detergent solution, such as an ionic or nonionic detergent solution. In certain modes of operation, the ECM material will be treated with an aqueous solution of sodium dodecyl sulfate (SDS) or another ionic or non-ionic detergent at a detergent concentration of about 0.05% to about 1%, more preferably about 0.05% to about 0.3%. This treatment can be for a period of time effective to disrupt cell and nuclear membranes and to reduce the immuno-globulin (e.g. IgA) content of the ECM material, typically in the range of about 0.1 hour to about 10 hours, more typically in the range of about 0.5 hours to about 2 hours.

In addition to treating an ECM material with a detergent medium, the ECM material can be contacted with other agents that participate in achieving the desired ECM component profile. For example, the ECM material can be treated with an aqueous medium, preferably basic, in which DNA is soluble. Such a medium can in certain forms have a pH in the range of above 7 to about 9, with pHs in the range of about 8 to about 8.5 proving particularly beneficial in some embodiments. The basic aqueous medium can include a buffer, desirably a biocompatible buffer such as tris(hydroxymethyl)aminomethane (TRIS), and/or a chelating agent such as ethylene diamine tetraacetic acid (EDTA). In one preferred form, the nucleic acid solubilizing medium is a TRIS-borate-EDTA (TBE) buffer solution. In another preferred form, the nucleic acid solubilizing medium is a solution of ammonium hydroxide. This treatment with a DNA solubilizing medium can be for a period of time effective to reduce the DNA content of the ECM material, typically in the range of about 0.1 hour to about 10 hours, more typically in the range of about 0.5 hours to about 2 hours.

In addition to treatment with detergent and DNA-solubilization media, ECM materials can be treated with a liquid medium that results in a substantial reduction of the level of lipid components of the ECM material. For example, the resulting native lipid content of the ECM material can be reduced to no greater than about 4% in certain embodiments. This can be accomplished, for example, by a preparative process that involves a step of treating the ECM material with a liquid organic solvent in which the lipids are soluble. Suitable such organic solvents include for example water-miscible solvents, including polar organic solvents. These include low molecular weight (e.g. $C_1$ to $C_4$) alcohols, e.g. methanol, ethanol, isopropanol, and butanols, acetone, chloroform, and others. Additional organic solvents include nonpolar solvents such as hexane, benzene, toluene and the like. In more preferred embodiments, the processed ECM material will be processed to have a native lipid content no greater than about 3%, or no greater than about 2.5%. This treatment with a lipid-removing medium can be for a period of time effective to reduce the lipid content of the ECM material, typically in the range of about 0.1 hour to about 10 hours, more typically in the range of about 0.1 hours to about 1 hour.

The ECM material can also be treated with a disinfecting solution. The disinfecting solution can include a disinfecting agent such as an alcohol, a peroxy compound, or another oxidizing or non-oxidizing disinfectant. In certain forms, the disinfecting solution will be a peracetic acid solution having a peracetic acid concentration of about 0.1% to about 0.3%. Peracetic acid and other oxidizing disinfectant treatment solutions such as those described in U.S. Pat. No. 6,206,931 can be used, for example.

The ECM material for use in the invention can retain native proteins and/or other materials from the source tissue, for instance biotropic agents, in their bioactive form. For example, the ECM material, after processing to render it acellular, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

In addition to sheet forms ECM material, the present invention contemplates the use of flowable compositions of ECM material and three-dimensional shapes of ECM material to isolate lung segments. An example of flowable ECM material can be comprised of an ECM gel as described in U.S. application Ser. No. 11/851,923 filed Sep. 7, 2007 and published May 8, 2008 as U.S. Patent Application Publication No. 20080107750, the disclosure of which is incorporated herein by reference in its entirety. Gel compositions for use in the invention can be prepared from an isolated ECM material, for example one of those disclosed above. The ECM material can be used to prepare a solubilized mixture including components of the starting material. This can be achieved for example by digestion of the ECM material in an acidic or basic medium and/or by contact with an appropriate enzyme or combination of enzymes.

Typically, the ECM material is reduced to particulate form to aid in the digestion step. This can be achieved by tearing, cutting, grinding or shearing the isolated ECM material. Illustratively, shearing may be conducted in a fluid medium, and grinding may be conducted with the material in a frozen state. For example, the material can be contacted with liquid nitrogen to freeze it for purposes of facilitating grinding into powder form. Such techniques can involve freezing and pulverizing submucosa under liquid nitrogen in a hammer mill.

Any suitable enzyme may be used for an enzymatic digestion step. Such enzymes include for example serine proteases, aspartyl proteases, and matrix metalloproteases. The concentration of the enzyme can be adjusted based on the specific enzyme used, the amount of submucosa to be digested, the duration of the digestion, the temperature of the reaction, and the desired properties of the final product. In one embodiment about 0.1% to about 0.2% of enzyme (pepsin, for example) is used and the digestion is conducted under cooled conditions for a period of time sufficient to substantially digest the ECM material. The digestion can be conducted at any suitable temperature, with temperatures ranging from 4-37° C. being preferred. Likewise, any suitable duration of digestion can be used, such durations typically falling in the range of about 2-180 hours. The ratio of the concentration of ECM material (hydrated) to total enzyme usually ranges from about 25 to about 125 and more typically the ratio is about 50, and the digestion is conducted at 4° C. for 24-72 hours. When an enzyme is used to aid in the digestion, the digestion will be performed at a pH at which the enzyme is active and more advantageously at a pH at which the enzyme is optimally active. Illustratively, pepsin exhibits optimal activity at pH's in the range of about 2-4. As an alternative to the use of an enzyme for digesting, acid digestion, for example using hydrochloric acid or acetic acid, can be used. In this manner, the resulting preparation can be free of the digestive enzyme, and upon neutralization with NaOH can form non-toxic materials.

The enzymes or other disruptive agents used to solubilize the ECM material can be removed or inactivated before or during the gelling process so as not to compromise gel formation or subsequent gel stability. Also, any disruptive agent, particularly enzymes, that remain present and active during storage of the tissue will potentially change the composition and potentially the gelling characteristics of the solution. Enzymes, such as pepsin, can be inactivated with protease inhibitors, a shift to neutral pH, a drop in temperature below 0° C., heat inactivation or through the removal of the enzyme by fractionation. A combination of these methods can be utilized to stop digestion of the ECM material at a predetermined endpoint, for example the ECM material can be immediately frozen and later fractionated to limit digestion.

For preparation of the flowable ECM composition, the ECM material can be enzymatically digested for a sufficient time to produce a hydrolysate of ECM components. The ECM can be treated with one enzyme or with a mixture of enzymes to hydrolyze the structural components of the material and prepare a hydrolysate having multiple hydrolyzed components of the starting ECM material. The length of digestion time is varied depending on the application, and the digestion can be extended to completely solubilize the ECM material. In some modes of operation, the ECM material will be treated sufficiently to partially solubilize the material to produce a digest composition comprising hydrolyzed ECM components and nonhydrolyzed ECM components. The digest composition can then optionally be further processed to remove at least some of the nonhydrolyzed components. For example, the nonhydrolyzed components can be separated from the hydrolyzed portions by centrifugation, filtration, or other separation techniques known in the art. In other aspects, the digest composition is not processed to remove the nonhydrolyzed components prior to use, and in certain embodiments is not processed to remove any components resulting from the digestion, prior to use.

ECM gel compositions for use in the present invention can optionally be prepared from enzymatically digested vertebrate ECM material that has been fractionated under acidic conditions, for example including pH ranging from about 2 to less than 7, especially to remove low molecular weight components. Typically for these purposes, the ECM hydrolysate is fractionated by dialysis against a solution or other aqueous medium having an acidic pH, e.g. a pH ranging from about 2 to about 5, more desirably greater than 3 and less than 7. In addition to fractionating the hydrolysate under acidic conditions, the ECM hydrolysate is typically fractionated under conditions of low ionic strength with minimal concentrations of salts such as those usually found in standard buffers such as PBS (i.e. NaCl, KCl, $Na_2HPO_4$, or $KH_2PO_4$) that can pass through the dialysis membrane and into the hydrolysate. Such fractionation conditions work to reduce the ionic strength of the ECM hydrolysate and thereby provide enhanced gel forming characteristics.

In accordance with one embodiment, the fractionated ECM hydrolysate will exhibit the capacity to gel upon adjusting the pH of a relatively more acidic aqueous medium containing it to about 5 to about 9, more preferably about 6.6 to about 8.0, and typically about 7.2 to about 7.8, thus inducing fibrillogenesis and matrix gel assembly. In one embodiment, the pH of the fractionated hydrolysate is adjusted by the addition of a buffer that does not leave a toxic residue, and has a physiological ion concentration and the capacity to hold physiological pH. Examples of suitable buffers include PBS, HEPES, and DMEM. In one embodiment the pH of the fractionated ECM hydrolysate is raised by the addition of a buffered NaOH solution to 6.6 to 8.0, more preferably 7.2 to 7.8. Any suitable concentration of NaOH solution can be used for these purposes, for example including about 0.05 M to about 0.5 M NaOH. In accordance with one embodiment, the ECM hydrolysate is mixed with a buffer and sufficient 0.25 N NaOH is added to the mixture to achieve the desired pH. If desired at this point, the resultant mixture can be aliquoted into appropriate forms or into designated cultureware and incubated at 37° C. for 0.5 to 10 hours to form an ECM gel.

The ECM gel can retain native proteins and/or other materials from the starting ECM material, for instance biotropic agents, in their bioactive form. For example, the ECM gel may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Additional components can be added to the hydrolysate composition before, during or after forming the gel. For example, proteins carbohydrates, growth factors, therapeutics, bioactive agents, nucleic acids, cells, pharmaceuticals, or radiopaque materials can be added. Examples of radiopaque materials include iodinated organic compounds, metal particles such as tantalum particles, bismuth thiol, bismuth subgallate, bismuth subsalicylate, bismuth tribromophenate, or bismuth sulfide. In certain embodiments, such materials are added prior to formation of the gel. This may be accomplished for example by forming a dry mixture of a powdered ECM hydrolysate with the additional component(s) in solid, dry form, and then reconstituting and gelling the mixture, or by incorporating the additional component(s) into an aqueous, ungelled composition of the ECM hydrolysate before, during (e.g. with) or after addition of the neutralization agent. In other embodiments, the additional component(s) are added to the formed ECM gel, e.g. by infusing or mixing the component(s) into the gel and/or coating them onto the gel.

In some embodiments of the invention, a particulate ECM material will be used. For example, a particulate ECM material can be added to an ECM hydrolysate composition, which particulate ECM material will then be incorporated in the formed gel. Particulate ECM materials can be prepared by cutting, tearing, grinding or otherwise comminuting an ECM starting material such as any of those described hereinabove, for example in some embodiments to form a randomly fragmented ECM particulate material. For example, a particulate ECM material having an average particle size of about 50 microns to about 500 microns may be included in the hydrolysate, more preferably about 100 microns to about 400 microns. The ECM particulate can be added in any suitable amount relative to a liquid carrier, such as the ECM hydrolyzate. When the ECM hydrolyzate is used, preferred ECM particulate to ECM hydrolysate weight ratios (based on dry solids) are about 0.1:1 to about 200:1, more preferably in the range of 1:1 to about 100:1. The inclusion of such ECM particulates in the ultimate ECM gel or other carrier material can serve to provide additional material that can function to provide bioactivity to the gel or other carrier (e.g. the particulate ECM including FGF-2 and/or other growth factors or bioactive substances as discussed herein) and/or serve as scaffolding material for tissue ingrowth. In addition to or as an alternative to an ECM hydrolysate carrier, other carriers may be used for an ECM particulate. For example, aqueous mediums, gellable or otherwise hardenable flowable polymeric compositions, fibrin glue, or other flowable carriers in which the ECM particles can be suspended can be used. As well, these other carriers may be used alone, or in combination with the ECM hydrolysate, to form the flowable ECM composition used in aspects of the present invention.

In further embodiments, a chemical crosslinking agent can be added to the ECM gel material (with or without ECM particulate as noted above) before, during or after delivery to the patient. Illustratively, a chemical crosslinking agent such as glutaraldehyde, formaldehyde, or a carbodiimide such as 1-ethyl-3-(3-dimethylaminopropyl)carbodiimide hydrochloride (EDC) can be mixed with the ECM gel material immediately prior to or during delivery to the patient, and the gel material can be delivered to an airway of a lung prior to its crosslinking-induced hardening to a non-flowable or less-flowable condition. In addition or alternatively, the flowable ECM gel material can be foamed immediately prior to or during delivery to an airway of the lung, for example by the introduction of air or other gas bubbles. Bubbles can be introduced for example by mechanical techniques such as aeration and/or by chemical foaming agents added to or included in the gel material. In still further embodiments, the crosslinked ECM gel material, either in foamed or non-foamed form, may alternatively be lyophilized or otherwise dried into a porous plug construct prior to delivering to the airways and used for occlusion of the targeted branch, e.g. as described elsewhere herein in relation to the use of ECM containing plugs.

It is within the knowledge of those of ordinary skill in the art to make three-dimensional shapes of previously described ECM material. The present invention contemplates the use of those materials as well as the more recently disclosed porous matrix materials, an example of which is disclosed in U.S. application Ser. No. 12/489,199 filed Jun. 22, 2009 and published on Dec. 31, 2009 as US20090326577, the disclosure of which is incorporated herein by reference in its entirety.

Three-dimensionally stable porous matrix materials, such as resilient foam or sponge form materials incorporating ECM material, can be included in graft materials used to practice the present invention. Illustrative sponge or foam matrices and methods for their preparation are disclosed, for example, in U.S. application Ser. No. 12/489,199 filed Jun. 22, 2009, published as US20090326577 on Dec. 31, 2009, which is hereby incorporated herein in its entirety.

Further in this regard, in certain forms, expanded ECM materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a material for use in the present invention. Illustratively, the expanded material can be enriched with bioactive components, dried, and/or molded, etc., in the formation of a material of a desired shape, configuration or consistency. In certain embodiments, a dried ECM construct formed with the expanded ECM material can be highly compressible (or expandable) such that the material can be compressed for delivery, such as from within the lumen of a cannulated delivery device, and thereafter expand upon deployment from the device so as to become anchored at the site of deployment within a patient.

Expanded collagenous or ECM materials can be formed by the controlled contact of a collagenous or ECM material with an aqueous solution or other medium containing sodium hydroxide. Notably, such treatment can be used to promote substantial expansion (i.e., greater than about 20% expansion. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. It will be apparent to one skilled in the art that the magnitude of the expansion is related to several factors, including for instance the concentration or pH of the alkaline medium, the exposure time of the alkaline medium to the material, and temperature used in the treatment of the material to be expanded, among others. These factors can be varied through routine experimentation to achieve a material having the desired level of expansion, given the disclosures herein.

A collagen fibril is comprised of a quarter-staggered array of tropocollagen molecules. The tropocollagen molecules themselves are formed from three polypeptide chains linked together by covalent intramolecular bonds and hydrogen bonds to form a triple helix. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein will not significantly disrupt the intramolecular and intermolecular bonds, but will denature the material to an extent that provides to the material a processed thickness that is at least twice the naturally-occurring thickness.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

With respect to the alkaline substance used to prepare an expanded remodelable collagenous material, any suitable alkaline substance generally known in the art can be used. Suitable alkaline substances can include, for example, salts or other compounds that that provide hydroxide ions in an aqueous medium. Preferably, the alkaline substance comprises sodium hydroxide (NaOH). Illustratively, the concentration of the alkaline substance for treatment of the remodelable material can be in the range of about 0.5 to about 2 M, or about 0.5 to 4 M, with a concentration of about 1 M to about 3 M commonly being used. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 3 M solution of NaOH having a pH of 14 at a temperature of about 37° C. for about 1.5 to 2 hours. Such treatment results in collagen denaturation and a substantial expansion of the remodelable material, for example to at least about twice its original volume. As indicated above, these processing steps can be modified to achieve the desired level of expansion. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct. If the expanded ECM material remains in a sheet form, it can be comminuted, for example by shearing with a rotating blade while suspended in a liquid medium such as water. The comminuted mixture can then be used, with or without modification, as a castable material to be charged to a mold and dried to form an ECM foam material. Such an ECM foam material can be crosslinked with a suitable chemical crosslinking agent, such as a glutaraldehyde, formaldehyde, or a carbodiimide crosslinking agent such as.

A starting ECM material (i.e., prior to treatment with the alkaline or other collagen-denaturing substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans. Accordingly, the treatment of a remodelable collagenous material with an alkaline substance as described herein can cause the material to expand to at least about twice its original volume, can alter the surface and/or porosity characteristics of the material, and can deplete the material of certain bioactive components. In some embodiments, this is accomplished while maintaining the material as an intact collagenous sheet, wherein the sheet can be further processed into any of a variety of medical materials and/or devices. Further, the remodelable collagenous material, such as an ECM sheet, can be treated with the alkaline medium so as to expand it as described herein, while the material retains an amount of a growth factor such as FGF-2, or another bioactive component such as fibronectin and/or heparin, that is/are native to the source tissue for the ECM.

In addition to or as an alternative to the inclusion of native bioactive components in the ECM material, non-native bioactive components including those synthetically produced by recombinant technology or other methods, may be incorporated into the expanded ECM material. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the expanded ECM materials used in the invention include, for example, antibiotics, thrombus-promoting substances such as blood clotting factors, e.g. thrombin, fibrinogen, and the like. As with the bioactive components previously described, these substances may be applied to the expanded ECM material as a premanufactured step, immediately prior to the procedure (e.g. by soaking the material in a solution containing a suitable antibiotic such as cefazolin), or during or after engraftment of the material in the patient.

An expanded ECM material may also exhibit an angiogenic character and thus be effective to induce angiogenesis in a host engrafted with the material. Angiogenic growth factors are well known in the art and include, for example, angiogenin, angiopoietin-1, Del-1, fibroblast growth factors (both acidic and basic), follistatin, granulocyte colony-stimulating factor, hepatocyte growth factor, interleukin-8 (IL-8), leptin, midkine, placental growth factor, platelet derived growth factor (PDGF), pleiotrophin, proliferin, transforming growth factors (both alpha and beta), tumor necrosis growth factor, and vascular endothelial growth factor (VEGF). Angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

An expanded ECM material can be provided in any suitable form, including a flowable aqueous composition (e.g., a fluidized composition), a powder, a gel, a sponge, one or more sheets, or a cast body. In forming a cast body, a solution and/or suspension containing the expanded ECM can be employed as a moldable or castable material in the formation of a foam body. The cast material can be dried directly without chemical crosslinking or can be crosslinked with a suitable crosslinking agent while cast in the mold, or can be dried and then crosslinked. Illustrative crosslinking agents for these purposes include glutaraldehyde, formaldehyde, carbodiimides, UV irradiation, or other crosslinking agents.

Turning now to the various Figures of the application, FIG. 1 provides a sectional view of the bronchial tubes of the human respiratory system. At the approximate level of the sternal angle, the trachea 20 bifurcates or splits into the right primary bronchus 21 (also called the right main bronchus) and the left primary bronchus 22 (also called the left main bronchus). Each bronchus runs freely for a few centimeters, and then enters its respective lung. Air is conducted through the primary bronchi into and out of each lung. After entering a lung, the primary bronchi each divide into secondary bronchi 25-29. The secondary bronchi are also known as lobar bronchi because each one directly conducts air to and from one of the lungs' five lobes. Within a lobe, tertiary bronchi 31-50 branch from the secondary bronchi. Each tertiary bronchus conducts air to and from a bronchopulmonary segment, which is an anatomical and functional division of a lobe. There are ten bronchopulmonary segments in the right lung and ten in the left, though some consider the left lung to have only eight due to the fusion of two sets of tertiary bronchi in the left lung, 41 and 42, as well as 47 and 48. Because they conduct air in and out the bronchopulmonary segments, the tertiary bronchi are also known as segmental bronchi. The tertiary bronchi then subdivide further into bronchioles (not shown). As used in this specification, the term "bronchial tube" refers to a bronchus or any of its secondary or tertiary branches. As used in this specification, the term "airway" refers to a bronchus, any of its secondary or tertiary branches, and the bronchioles to which these bronchial tubes open or communicate.

Figure 2:
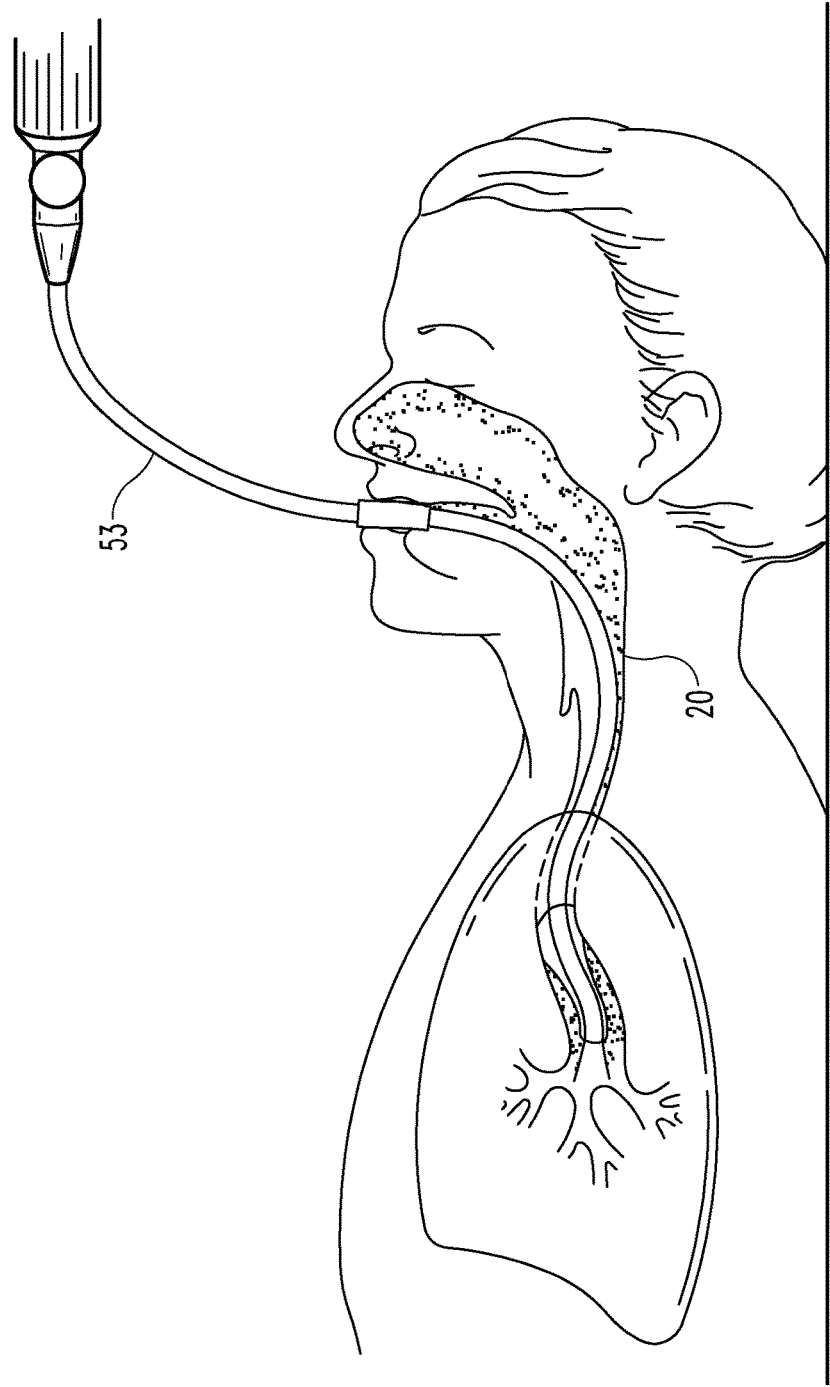
FIG. 2 is a simplified sectional view of the thorax and an illustration of a bronchoscope accessing the lumen of the bronchial tubes.

The method of the present invention may be performed using bronchoscopy. Bronchoscopy is a technique of visualizing the inside of the airways for diagnostic and therapeutic purposes. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's tip; and a tube (commonly called a working channel) through which instruments and therapeutic agents may be inserted and placed into the lungs. The distal tip of a bronchoscope is steerable. Rotating a lever placed at the handle of the bronchoscope actuates a steering mechanism which deflects the tip in one or more directions. As shown in FIG. 2, the bronchoscope 53 is usually inserted through the nose or mouth, or occasionally through a tracheostomy (not shown), then through the lumen of the trachea and the lumens of the bronchial tubes. During a typical procedure, the bronchoscopist holds the bronchoscope with one hand and the bronchoscope tube with the other hand. He or she manipulates the distal tip of the bronchoscope inside the lung by rotating a deflection lever and by pushing and pulling the tube. Once the tip is brought to a target location, a bronchoscopic tool or therapeutic material can be inserted into the working channel.

In general, the apex portion of upper lung lobes are most often affected by disease such as COPD (Chronic Obstructive Pulmonary Disease). The following description thus describes treating one of these lung segments. This should, however, not be viewed as limiting the present invention. As one of ordinary skill will recognize, the present invention may be applied to occlude or block any airway, and particularly any bronchial tube, to treat other portions of the lung.

Figure 3:
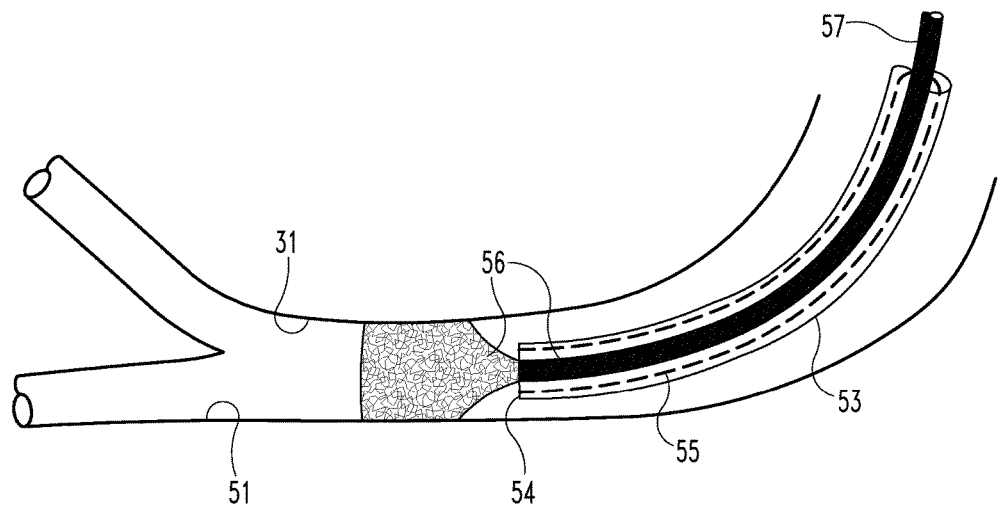
FIG. 3 is an enlarged, partial sectional view of a tertiary bronchus, its bronchioles, and an illustration of the distal end of a bronchoscope and ECM material according to one embodiment of the present invention.

Referring back to FIG. 1, the medical practitioner locates the distal tip 54 of the bronchoscope 53 into the lumen of the target bronchial tube, here, the lumen 51 of tertiary bronchus 31. An enlarged cross-section of tertiary bronchus 31 and distal tip 54 of bronchoscope 53 is shown in FIGS. 3, 6, 7, and 8. Referring first to FIG. 3, the medical practitioner typically inserts a long hollow tube 57 through working channel 55 (or tube 55), and then delivers ECM material 56 from the hollow tube 57, and out distal tip 54. This ECM material can be in flowable form, in plug form, or a combination thereof, for example. As ECM material 56 exits distal tip 54, the medical practitioner allows the ECM material to pool and/or lodge in the lumen until a sufficient amount of ECM material resides within the lumen of the bronchial tube to occlude, and thus block, the lumen. The medical practitioner then stops delivering ECM material into the lumen and removes the bronchoscope and hollow tube 57 from the patient. It is also contemplated by the present invention that the medical practitioner could deliver the ECM material(s) directly through the working channel 55 (or tube 55) without using long hollow tube 57 as a sleeve to the line the inside of working channel 55. It is further contemplated that conventional bronchoscopes can be modified to include or support additional lumens, for example at least one lumen for delivering a flowable or other ECM composition, and at least a second lumen for delivering a plug comprising an ECM material. As well, the flowable or other ECM composition can be delivered in a lumen separate from the bronchoscope, for example through a separate catheter. In certain modes of practice, a flowable ECM composition can first be delivered into the lung using a first lumen, and a plug comprising an ECM or other suitable matrix material can then be delivered to and lodged in a position proximal of the flowable ECM, for example to facilitate retention of the location of the flowable ECM material in a passageway(s) distal of the lodged plug. Additionally or alternatively, prior to, during, or after delivery of the flowable or other ECM material to an airway region of the lung, the airway region can be treated mechanically or chemically to initiate a healing response in the region, which may be used to facilitate the development of new tissue of the patient in the region in combination with the delivered flowable or other ECM material. Such treatment can, for example, include debridement with a brush or other suitable instrument, and can in certain modes initiate bleeding in the treated region.

A presently preferred embodiment of flowable ECM material to use in embodiments of the invention is the previously described ECM gel. The preferable properties of the ECM gel is that it has a low viscosity when delivered and then increases in viscosity to remain in place in the bronchial tube targeted for occlusion. Illustratively, the ECM gel can increase in viscosity when transitioning from a temperature below body temperature of the patient to a body temperature of the patient (e.g. about 37 degrees C. for a human patient). The ECM gel may also preferably include other materials to promote atelactasis such as a sclerosing agent. ECM particles or antimicrobial or antibiotic agents can also be added to the gel, for example to promote healing and prevent infection.

Figure 4:
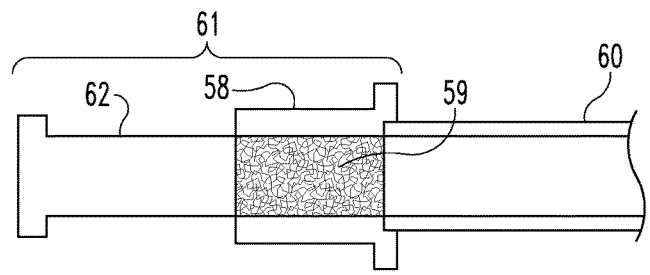
FIGS. 4 and 5 are enlarged sectional views of an ECM plug loader and the distal end of a plug introducer.
Figure 5:
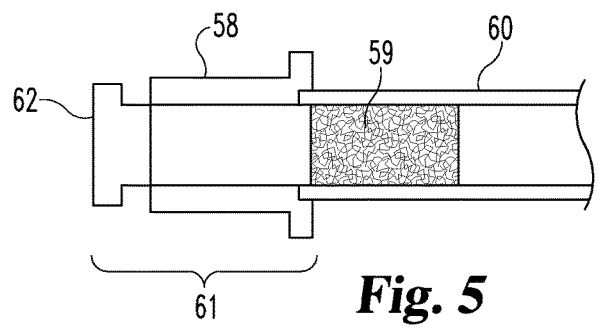

Another preferred embodiment of the present invention is to use expandable ECM plugs to block the lumen of the bronchial tube. Referring to FIGS. 4 and 5, a compressed foam plug of ECM material 59 is loaded into the distal end of a long hollow tube 60 (or plug introducer 60). An open cylinder 58 of loader 61 containing the compressed ECM material 59 is placed against the distal tip of plug introducer 60. The plunger 62 on the loader 61 is then pushed inside the cylinder 58 to displace the expandable ECM plug from the cylinder 58 and load it into the plug introducer 60.

Figure 6:
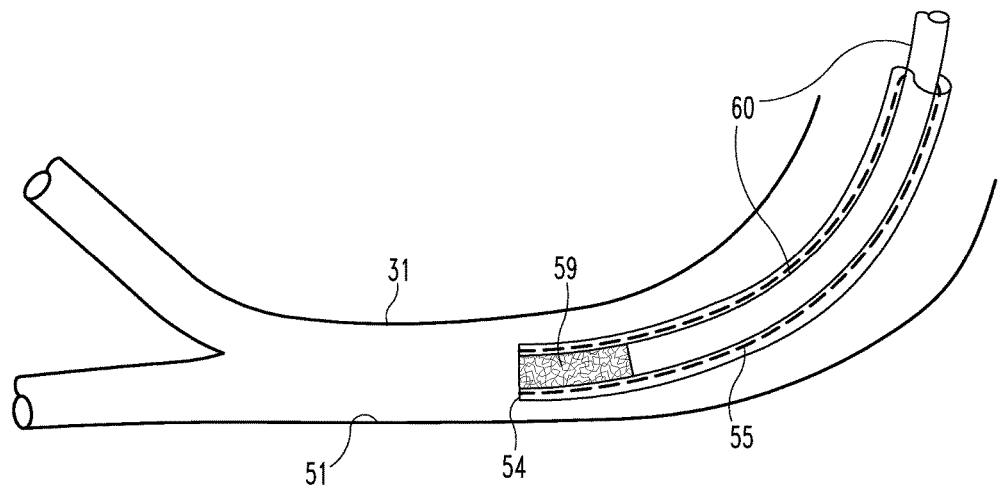
FIGS. 6, 7, and 8 are enlarged, partial sectional views of a tertiary bronchus, its bronchioles, and an illustration of the distal end of a bronchoscope and ECM material according to another embodiment of the present invention.
Figure 7:
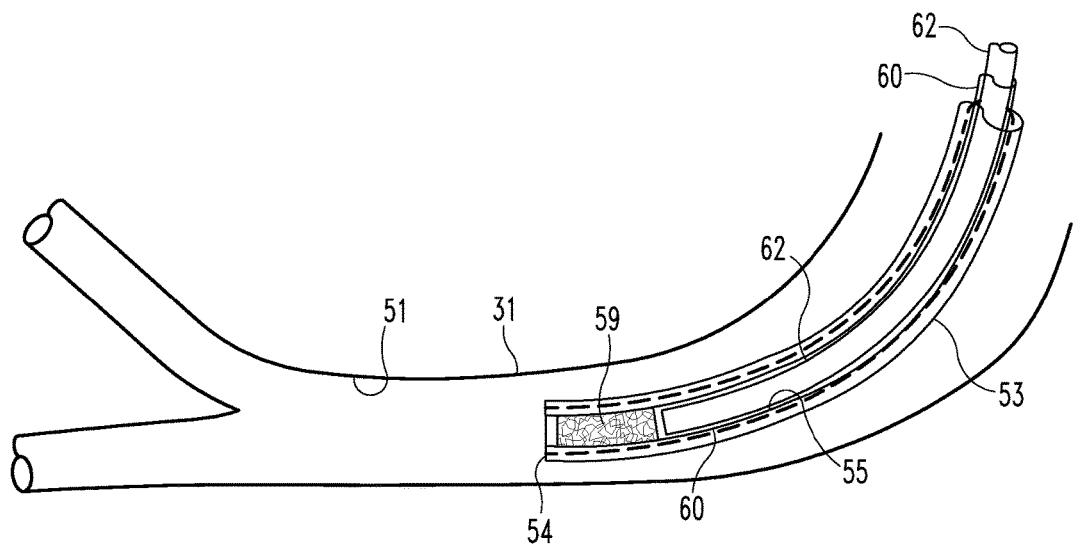
Figure 8:
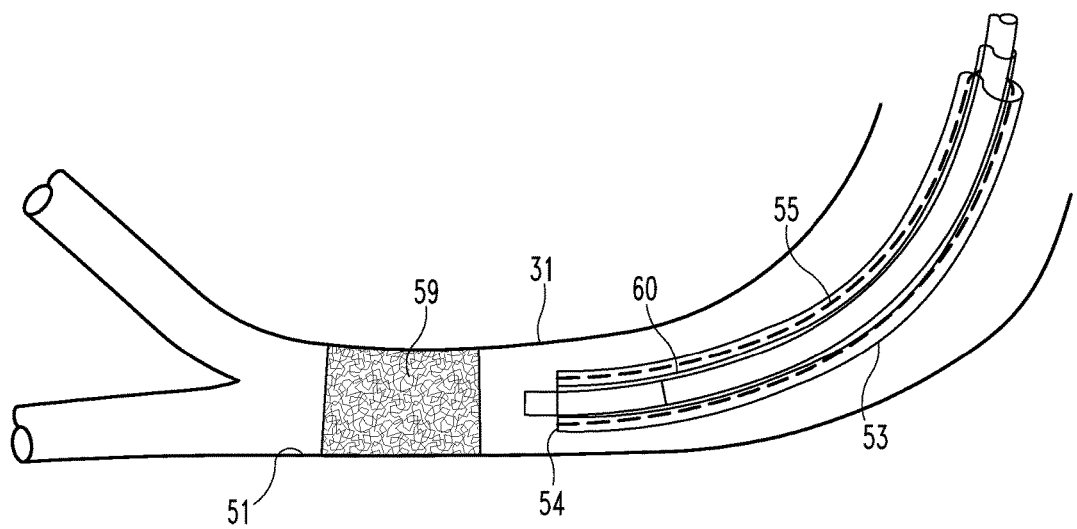

FIG. 6 depicts an enlarged cross-section of the distal tip 54 of bronchoscope 53 located in the lumen of the target bronchial tube, here again, the lumen 51 of tertiary bronchus 31. The distal tip 54 is placed into position by the medical practitioner as previously described. The long hollow tube 60 (or plug introducer 60) is then placed through the working channel 55 in the bronchoscope, preferably stopping at or near the distal tip 54 of the bronchoscope. Referring to FIG. 7 and with the distal tip 54 located in the desired position in the lumen 51 of the bronchial tube 31, the medical practitioner inserts a plunger 62 into the proximal end (not shown) of the plug introducer 60 to push the expandable ECM plug 59 out the distal tip 54 and into the lumen 51 of the bronchial tube 31. Referring to FIG. 8, upon exiting the plug introducer 60, the compressed ECM plug 59 expands, for example by swelling upon fluid uptake, thus occluding the lumen of the bronchial tube. Optionally, as discussed above, the plug 59 can be used in combination with a flowable ECM composition, for example being implanted proximal to an amount of previously introduced, flowable ECM composition. After placement of the plug, the medical practitioner then removes the plunger 62, plug introducer 60 and bronchoscope from the patient.

A presently preferred embodiment of expandable ECM material to use in this embodiment of the invention is the previously described resilient foam form of ECM materials. The expansion characteristics can be modified by adding a crosslinking agent, such a carbodiimide. The ECM plugs can also be loaded with therapeutic agents such as antimicrobials and antibiotics. To facilitate anchoring into the lumen of the bronchial tube, the outer surface of the compressed ECM plug could also be coated with water activated adhesive such as gelatin/fructose adhesive or fibrin glue.

Another embodiment of the present invention contemplates that the ECM plug will have a one-way valve. The valve would allow air or mucus from the occluded lung to be released but not allow any new air to enter the occluded lung. Examples of ECM plugs with one-way valves are depicted in FIGS. 9-12. The plugs are shown in their expanded, non-compressed state.

Figure 9:
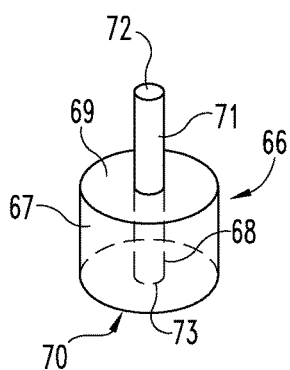
FIGS. 9, 10, 11, and 12, are perspective views of plugs made of ECM material incorporating a one-valve according to other embodiments of the present invention.

Referring first to FIG. 9, plug 66 includes a body 67 having a generally cylindrical shape and a passageway 68 extending and open between face 69 and face 70. A tube 71 with two open ends 72 and 73 resides in passageway 68. When inserted in an airway or bronchial tube, face 70 is oriented toward the portion of lung being isolated so that air or mucous could enter open end 73 and exit open end 72. Body 67 is preferably made of the previously described foam or sponge forms of ECM material, while tube 71 is preferably made of generally flat ECM material. It is well within the knowledge of the art to fabricate these three-dimensional shapes from the previously described ECM materials.

Figure 10:
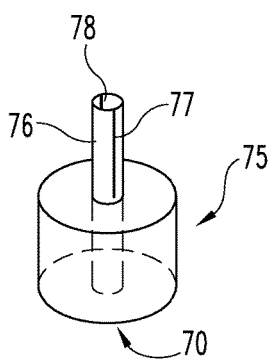

The plug 75 shown in FIG. 10 is largely of the same construction as the plug 66 shown in FIG. 9. The difference, however, resides in tube 76, where lengthwise slots 77 and 78 are cut through the walls of tube 76.

Figure 11:
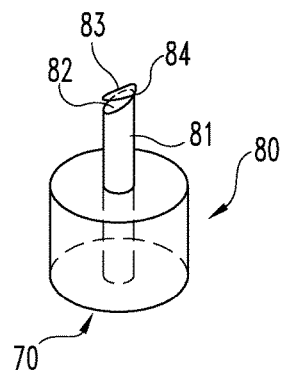

The plug 80 shown in FIG. 11 is also largely of the same construction as the plug 66 shown in FIG. 9. The difference, however, resides in the open end 82 of tube 81. Open end 82 is at least partially covered by a normally-closed tongue 83. Tongue 83 is preferably made of the same material as tube 81 and is attached to tube 81 with a living hinge 84.

Figure 12:
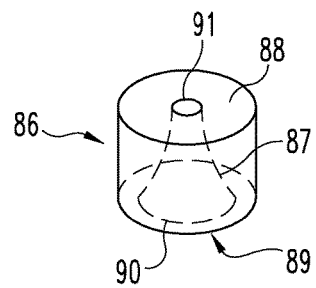

Referring to FIG. 12, The plug 86 includes a body 67 having a generally cylindrical shape and a passageway 87 extending and open between face 88 and face 89. Passageway 87 has a general frustoconical shape with opening 90 in face 89 larger than opening 91 in face 88. When inserted in an airway or bronchial tube, face 89 is oriented toward the portion of the lung being isolated so that air or mucous could enter open end 89 and exit open end 88.

A variety of other plugs comprised of ECM material may be used within the present invention. The plugs can as examples be manufactured from intact ECM sheet materials or can be cast or molded structures made with ECM materials. The plugs can have a variety of shapes as desired to meet particular applications.

As disclosed above, an ECM material introduced into the patient can lead to patient tissue growth within the lung. Such tissue growth can reduce the operable volume of the lung, for example by occluding or blocking an airway, and particularly a bronchial tube. The ingrown patient tissue is characterized by new patient collagenous extracellular matrix deposition and the presence of viable patient fibroblasts in the newly formed extracellular matrix. The ingrown patient tissue can also include bronchus associated lymphoid tissue. The new patient tissue can occupy a volume that was previously part of the open, operable internal volume of the patient's lung or lungs. The occupied volume can be a terminal volume that previously formed an outer periphery of the open, operable internal volume, or can be an intermediate volume that effectively cuts off or fluidly isolates a remaining open volume of the lung that exists beyond the ingrown tissue occlusion.

For the purpose of promoting a further understanding of aspects of the invention, the following specific Examples are provided. It will be understood that these Examples are illustrative, and not limiting, in nature.

Example 1

In this Example, flowable ECM compositions were introduced into the lungs of sheep, after which histology was performed 1 to 2 months after initial treatment. The ECM compositions demonstrated the capacity to induce the development of patient tissue in the passageways of the lungs.

In particular, two different flowable ECM compositions were employed in the study. The compositions were prepared as generally described in U.S. Pat. No. 8,021,692 issued Sep. 20, 2011, each flowable composition including an aqueous gel of hydrolyzed small intestinal submucosa (SIS) and suspended comminuted SIS particles. For one composition, the comminuted SIS particles were unfractionated, and in another the comminuted SIS particles were screened to have a size in the range of about 150-250 microns. Also, the iodinated radiopaque contrast agent, diatrizoic acid, was incorporated into the compositions in sufficient amount to render them radiopaque under X-ray imaging. The compositions were introduced into the sheep subjects during bronchoscopy, via a catheter affixed to the bronchoscope. Histology was performed as noted above, 1 to 2 months after implant. Newly developed and developing tissue was observed in the implant regions, which included bronchus associated lymphoid tissue.

Example 2

In this Example, cylindrical collagenous foam plugs receptive to tissue ingrowth were delivered into a targeted segment of the right cranial lobe of the lung of a sheep (cranial aspect of the cranial lobe). The collagenous foam plugs were prepared from SIS material that had been expanded by exposure to sodium hydroxide solution, rinsed, comminuted to form a material that was cast and dried by lyophilization in a mold, generally as described in United States Patent Application Publication No. 20090318934 dated Dec. 24, 2009, publishing U.S. patent application Ser. No. 12/488,974 filed Jun. 22, 2009. The formed plugs were crosslinked using 1-ethyl-3-(3-dimethylaminopropyl)carbodiimide hydrochloride (EDC). The targeted bronchiole was first debrided using mechanical debridement with a stainless steel brush to allow blood to be present in the airway to further hydrate the plugs. A total of 9 plugs were delivered; approximately 4 cm in length (3 cm to 5 cm) and crimped to fit into a 10Fr delivery system while expected to re-expand once hydrated to a diameter of approximately 0.5 cm. The purpose of this study was to demonstrate delivery and ability of the plugs to be retained in the targeted sub-segment without migration once the animal was revived for a period of 24 hours. Gross observations upon necropsy showed that all 9 plugs remained in the targeted subsegment and there was no evidence of migration. Further, it was observed that the plugs expanded to fit the contour of the airway, with the more proximal plugs being more expanded upon removal and the more distal plugs retaining more of the crimped diameter.

In further experiments, flowable ECM compositions as described in Example 1 are introduced into the targeted segment of the right cranial lobe, and the foam plugs are implanted behind (proximal to) the introduced flowable ECM compositions. The foam plugs themselves block segments of the lung and also will facilitate maintenance of the flowable ECM compositions in the desired region during new tissue development stimulated by the flowable ECM compositions.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

The invention claimed is:

1. A method for reducing lung volume, comprising delivering a flowable extracellular matrix material into an open lumen of the lung in an amount sufficient to occupy an open volume of the lumen and thereby occlude the lumen in a first region, and thereafter delivering a foam plug comprised of an extracellular matrix material to a position in the lumen proximal of the first region, wherein the foam plug expands to occlude the lumen at said position to facilitate retention of the flowable extracellular matrix material in the first region, and wherein the flowable extracellular matrix material leads to deposition of new collagenous extracellular matrix tissue of the patient that occupies the open volume of the lumen of the lung to block the lumen and thereby reduce a volume of the lung.

2. The method of claim 1, further comprising blocking the passage of air in the lumen of the airway with the flowable extracellular matrix material.

3. The method of claim 2, wherein the lumen of an airway is the lumen of a bronchial tube.

4. The method of claim 2, wherein the flowable extracellular matrix material includes an extracellular matrix gel, the method further comprising inserting a tube through the lumen of a primary bronchus, through the lumen of a secondary bronchus, and into the lumen of the airway, wherein the lumen of the airway opens to the portion of the lung that is to be isolated, and wherein said delivering includes flowing the flowable composition of extracellular matrix material through the tube.

5. The method of claim 4, wherein the lumen of the airway is the lumen of a tertiary bronchus.

6. The method of claim 1, wherein the flowable extracellular matrix material includes a sclerosing agent.

7. The method of claim 1, wherein the flowable extracellular matrix material includes an antibiotic.

8. The method of claim 1, wherein the flowable extracellular matrix material includes cells.

9. The method of claim 1, wherein the flowable extracellular matrix material includes a radiopaque material.

10. The method of claim 1, wherein the flowable extracellular matrix material comprises an extracellular matrix gel, and wherein the method also comprises, prior to said delivering a flowable extracellular matrix material, foaming the extracellular matrix gel by introducing gas into the extracellular matrix gel.

11. The method of claim 10, wherein the flowable extracellular matrix material includes a hydrolyzed extracellular matrix material.

12. The method of claim 1, wherein the flowable extracellular matrix tissue includes a comminuted extracellular matrix material.

13. The method of claim 1, wherein the flowable extracellular matrix material includes at least one growth factor native to a source tissue for the extracellular matrix tissue.

14. A method to reduce lung volume, comprising:
delivering a flowable extracellular matrix material into a portion of the lung so that the flowable extracellular matrix material pools in said portion of the lung;
locating a tube with a distal passageway in the lumen of an airway of the lung, wherein the lumen of the airway opens to said portion of the lung;
pushing a foam plug comprised of extracellular matrix material out the distal passageway and into the lumen of the airway, wherein the plug expands to fit a contour of an open volume of the lumen and thereby occlude the lumen and facilitate retention of the flowable extracellular matrix material in said portion of the lung, and wherein the plug is receptive to ingrowth of new tissue of the patient, the ingrowth of new tissue of the patient including deposition of new collagenous extracellular matrix of the patient.

15. The method of claim 14, wherein the lumen of an airway is the lumen of a bronchial tube.

16. The method of claim 15, further including blocking the bronchial tube with the plug.

17. The method of claim 15, wherein the lumen of the bronchial tube is the lumen of a tertiary bronchus.

18. The method of claim 14, wherein the extracellular matrix material of the plug is collagenous.

19. The method of claim 14, wherein the plug has an exterior surface, and at least a portion of the exterior surface is coated with a water-activated adhesive.

20. The method of claim 14, further comprising inserting the tube through the lumen of a primary bronchus, through the lumen of a secondary bronchus, and into the lumen of the bronchial tube.

21. The method of claim 14, wherein the plug includes a one-way valve.

22. The method of claim 14, wherein the flowable extracellular matrix material includes a radiopaque material.

23. The method of claim 1, also comprising treating tissue defining the lumen to initiate a healing response in the tissue.

* * * * *